(12) United States Patent
Deitz

(10) Patent No.: US 8,777,878 B2
(45) Date of Patent: Jul. 15, 2014

(54) DEVICES, SYSTEMS, AND METHODS FOR MEASURING AND EVALUATING THE MOTION AND FUNCTION OF JOINTS AND ASSOCIATED MUSCLES

(75) Inventor: Adam Deitz, San Francisco, CA (US)

(73) Assignee: AECC Enterprises Limited, Bournemouth, Dorset (GB)

( * ) Notice: Subject to any disclaimer, the term of this patent is extended or adjusted under 35 U.S.C. 154(b) by 50 days.

(21) Appl. No.: 13/362,337

(22) Filed: Jan. 31, 2012

(65) Prior Publication Data

US 2012/0130285 A1    May 24, 2012

Related U.S. Application Data

(63) Continuation of application No. 12/247,552, filed on Oct. 8, 2008, now abandoned.

(60) Provisional application No. 60/978,907, filed on Oct. 10, 2007, provisional application No. 60/981,922, filed on Oct. 23, 2007, provisional application No. 61/015,149, filed on Dec. 19, 2007, provisional application No. 61/054,426, filed on May 19, 2008.

(51) Int. Cl.
*A61B 5/00*    (2006.01)

(52) U.S. Cl.
USPC .......................................................... 600/595

(58) Field of Classification Search
USPC .................................................. 600/587, 595
See application file for complete search history.

(56) References Cited

U.S. PATENT DOCUMENTS

| | | |
|---|---|---|
| 3,678,190 A | 7/1972 | Cook |
| 4,210,317 A | 7/1980 | Spann et al. |
| 4,404,590 A | 9/1983 | Mayer et al. |
| 4,611,581 A | 9/1986 | Steffee |
| 4,803,734 A | 2/1989 | Onishi et al. |
| 4,805,602 A | 2/1989 | Puno et al. |
| 4,922,909 A | 5/1990 | Little et al. |
| 5,000,165 A | 3/1991 | Watanabe |

(Continued)

FOREIGN PATENT DOCUMENTS

| | | |
|---|---|---|
| AU | 2007238017 B2 | 4/2007 |
| DE | 20009875 U1 | 10/2000 |

(Continued)

OTHER PUBLICATIONS

Breen, et al. Quantitative analysis of lumbar spine intersegmental motion. European Journal of Physical Medicine and Rehabilitation. 1993; 3(5): 182-90.

(Continued)

*Primary Examiner* — Max Hindenburg
(74) *Attorney, Agent, or Firm* — Shartsis Friese LLP; Cecily Anne O'Regan

(57) ABSTRACT

Apparatuses are disclosed that is adapted and configured to cause and control joint motion of a patient. Apparatuses comprise, for example, a first motion member configured to engage a patient proximal to a target joint; a second motion member configured to engage a patient distal to a target joint; and a coupling member configured to connect the first motion member to the second motion member and further adapted to allow rotation of the first and second motion member around an axis, wherein the apparatus is engageable with a medical diagnostic device and further configured to capture patient specific data.

15 Claims, 8 Drawing Sheets

(56) References Cited

U.S. PATENT DOCUMENTS

| | | | |
|---|---|---|---|
| 5,019,081 A | 5/1991 | Watanabe | |
| 5,058,602 A | 10/1991 | Brody | |
| 5,090,042 A | 2/1992 | Bejjani et al. | |
| 5,099,859 A | 3/1992 | Bell | |
| 5,129,900 A | 7/1992 | Asher et al. | |
| 5,203,346 A | 4/1993 | Fuhr et al. | |
| 5,316,018 A * | 5/1994 | O'Brien | 600/595 |
| 5,320,640 A | 6/1994 | Riddle et al. | |
| 5,330,417 A | 7/1994 | Petersen et al. | |
| 5,349,956 A | 9/1994 | Bonutti | |
| 5,400,800 A | 3/1995 | Jain et al. | |
| 5,414,811 A | 5/1995 | Parulski et al. | |
| 5,427,116 A | 6/1995 | Noone | |
| 5,442,729 A * | 8/1995 | Kramer et al. | 704/271 |
| 5,443,505 A | 8/1995 | Wong et al. | |
| 5,445,152 A | 8/1995 | Bell et al. | |
| 5,474,555 A | 12/1995 | Puno et al. | |
| 5,505,208 A | 4/1996 | Toomim et al. | |
| 5,548,326 A | 8/1996 | Michael | |
| 5,575,792 A | 11/1996 | Errico et al. | |
| 5,582,186 A | 12/1996 | Wiegand | |
| 5,582,189 A | 12/1996 | Pannozzo | |
| 5,590,271 A | 12/1996 | Klinker | |
| 5,640,200 A | 6/1997 | Michael | |
| 5,643,263 A | 7/1997 | Simonson | |
| 5,683,392 A | 11/1997 | Richelsoph et al. | |
| 5,688,274 A | 11/1997 | Errico et al. | |
| 5,690,630 A | 11/1997 | Errico et al. | |
| 5,707,643 A | 1/1998 | Ogura et al. | |
| 5,715,334 A | 2/1998 | Peters | |
| 5,725,527 A | 3/1998 | Biedermann et al. | |
| 5,740,267 A | 4/1998 | Echerer et al. | |
| 5,741,255 A | 4/1998 | Krag et al. | |
| 5,748,703 A * | 5/1998 | Cosman | 378/152 |
| 5,755,675 A | 5/1998 | Sihvonen | |
| 5,772,592 A | 6/1998 | Cheng et al. | |
| 5,772,595 A | 6/1998 | Votruba et al. | |
| 5,784,431 A | 7/1998 | Kalend et al. | |
| 5,792,077 A | 8/1998 | Gomes | |
| 5,797,911 A | 8/1998 | Sherman et al. | |
| 5,810,006 A | 9/1998 | Votruba et al. | |
| 5,813,406 A * | 9/1998 | Kramer et al. | 600/595 |
| 5,824,072 A | 10/1998 | Wong et al. | |
| 5,838,759 A * | 11/1998 | Armistead | 378/57 |
| 5,863,293 A | 1/1999 | Richelsoph | |
| 5,879,350 A | 3/1999 | Sherman et al. | |
| 5,885,285 A | 3/1999 | Simonson | |
| 5,891,060 A | 4/1999 | McGregor et al. | |
| 5,891,145 A | 4/1999 | Morrison et al. | |
| 5,899,859 A | 5/1999 | Votruba et al. | |
| 5,931,781 A | 8/1999 | De Boer | |
| 5,954,674 A | 9/1999 | Fuhr | |
| 5,964,760 A | 10/1999 | Richelsoph | |
| 6,002,959 A | 12/1999 | Steiger et al. | |
| 6,010,503 A | 1/2000 | Richelsoph et al. | |
| 6,019,759 A | 2/2000 | Rogozinski | |
| 6,022,350 A | 2/2000 | Ganem | |
| 6,049,740 A | 4/2000 | Whitehead et al. | |
| 6,074,391 A | 6/2000 | Metz-Stavenhagen et al. | |
| 6,075,905 A | 6/2000 | Herman et al. | |
| 6,077,262 A | 6/2000 | Schlapfer et al. | |
| 6,090,111 A | 7/2000 | Nichols | |
| 6,132,430 A | 10/2000 | Wagner | |
| 6,141,579 A | 10/2000 | Bonutti | |
| 6,155,993 A | 12/2000 | Scott | |
| 6,248,105 B1 | 6/2001 | Schlapfer et al. | |
| 6,269,565 B1 | 8/2001 | Inbar et al. | |
| 6,276,799 B1 | 8/2001 | Van Saarloos et al. | |
| 6,280,395 B1 | 8/2001 | Appel et al. | |
| 6,290,703 B1 | 9/2001 | Ganem | |
| 6,298,259 B1 | 10/2001 | Kucharczyk et al. | |
| 6,351,547 B1 | 2/2002 | Johnson et al. | |
| 6,427,022 B1 | 7/2002 | Craine et al. | |
| 6,428,490 B1 * | 8/2002 | Kramer et al. | 600/595 |
| 6,434,264 B1 | 8/2002 | Asar | |
| 6,451,021 B1 | 9/2002 | Ralph et al. | |
| 6,469,717 B1 | 10/2002 | Wineke et al. | |
| 6,471,705 B1 | 10/2002 | Biedermann et al. | |
| 6,497,672 B2 * | 12/2002 | Kramer | 600/595 |
| 6,524,315 B1 | 2/2003 | Selvitelli et al. | |
| 6,540,749 B2 | 4/2003 | Schafer et al. | |
| 6,542,574 B2 | 4/2003 | Grodzins | |
| 6,547,790 B2 | 4/2003 | Harkey et al. | |
| 6,560,476 B1 | 5/2003 | Pelletier et al. | |
| 6,565,565 B1 | 5/2003 | Yuan et al. | |
| 6,608,916 B1 | 8/2003 | Wei et al. | |
| 6,608,917 B1 | 8/2003 | Wei et al. | |
| 6,697,659 B1 | 2/2004 | Bonutti | |
| 6,698,885 B2 | 3/2004 | Berger et al. | |
| 6,719,750 B2 | 4/2004 | Varner et al. | |
| 6,726,691 B2 | 4/2004 | Osorio et al. | |
| 6,866,643 B2 * | 3/2005 | Kramer | 600/595 |
| 6,882,744 B2 | 4/2005 | Oosawa | |
| 6,890,312 B1 * | 5/2005 | Priester et al. | 600/595 |
| 6,907,280 B2 | 6/2005 | Becerra et al. | |
| 6,963,768 B2 | 11/2005 | Ho et al. | |
| 6,964,781 B2 | 11/2005 | Brubaker et al. | |
| 6,990,368 B2 | 1/2006 | Simon | |
| 7,000,271 B2 | 2/2006 | Varadharajulu | |
| 7,034,063 B2 | 4/2006 | Nienhaus et al. | |
| 7,046,830 B2 | 5/2006 | Gerard et al. | |
| 7,050,537 B2 | 5/2006 | Tsujii | |
| 7,110,587 B1 | 9/2006 | Natanzon et al. | |
| 7,117,027 B2 | 10/2006 | Zheng et al. | |
| 7,127,090 B2 | 10/2006 | Kreang-Arekul et al. | |
| 7,133,066 B2 | 11/2006 | Bourret | |
| 7,153,307 B2 | 12/2006 | Scribner et al. | |
| 7,158,661 B2 | 1/2007 | Inoue | |
| 7,184,814 B2 | 2/2007 | Lang et al. | |
| 7,241,303 B2 | 7/2007 | Reiss et al. | |
| 7,243,387 B2 | 7/2007 | Schindler et al. | |
| 7,266,406 B2 | 9/2007 | Kroeckel | |
| 7,333,649 B2 | 2/2008 | Nagata et al. | |
| 7,343,635 B2 | 3/2008 | Jackson | |
| 7,502,641 B2 | 3/2009 | Breen | |
| 7,679,971 B1 | 3/2010 | Yu | |
| 7,747,309 B2 | 6/2010 | Prince | |
| 7,780,703 B2 | 8/2010 | Yuan et al. | |
| 7,837,635 B2 * | 11/2010 | Lissek et al. | 600/595 |
| 2002/0120272 A1 | 8/2002 | Yuan et al. | |
| 2003/0081837 A1 | 5/2003 | Williame et al. | |
| 2003/0086596 A1 | 5/2003 | Hipp et al. | |
| 2003/0220648 A1 | 11/2003 | Osorio et al. | |
| 2003/0225327 A1 | 12/2003 | Willen et al. | |
| 2004/0010260 A1 | 1/2004 | Scribner et al. | |
| 2004/0098803 A1 | 5/2004 | Schindler et al. | |
| 2004/0141591 A1 | 7/2004 | Izuhara | |
| 2004/0172145 A1 | 9/2004 | Varadharajulu | |
| 2004/0225296 A1 | 11/2004 | Reiss et al. | |
| 2005/0107681 A1 | 5/2005 | Griffiths | |
| 2005/0148948 A1 | 7/2005 | Caputa et al. | |
| 2005/0187459 A1 | 8/2005 | Trequattrini et al. | |
| 2005/0222505 A1 | 10/2005 | Damadian et al. | |
| 2005/0240193 A1 | 10/2005 | Layne et al. | |
| 2005/0259794 A1 | 11/2005 | Breen | |
| 2006/0020196 A1 | 1/2006 | Elias | |
| 2006/0149136 A1 | 7/2006 | Seto et al. | |
| 2006/0185091 A1 | 8/2006 | Jackson | |
| 2006/0264952 A1 | 11/2006 | Nelson et al. | |
| 2007/0067034 A1 | 3/2007 | Chirico et al. | |
| 2007/0287900 A1 | 12/2007 | Breen et al. | |
| 2008/0039867 A1 | 2/2008 | Feussner et al. | |
| 2008/0125678 A1 | 5/2008 | Breen | |
| 2009/0099481 A1 | 4/2009 | Deitz | |
| 2009/0285466 A1 | 11/2009 | Hipp et al. | |
| 2012/0321168 A1 | 12/2012 | Deitz | |

FOREIGN PATENT DOCUMENTS

| | | |
|---|---|---|
| EP | 804032 A2 | 10/1997 |
| EP | 1219240 A2 | 7/2002 |
| EP | 1219240 A3 | 11/2002 |
| EP | 1519681 B1 | 11/2006 |
| JP | 7284020 A2 | 10/1995 |

(56) References Cited

FOREIGN PATENT DOCUMENTS

| WO | WO01/93764 A1 | 12/2001 |
|---|---|---|
| WO | WO2004/004570 A1 | 1/2004 |
| WO | WO 2005/007217 A2 | 1/2005 |
| WO | WO2007/121337 A2 | 4/2007 |
| WO | WO2007/121337 A3 | 4/2007 |
| WO | WO2009/049062 A9 | 4/2009 |
| WO | WO2012/082615 A2 | 6/2012 |
| WO | WO 2012/082615 A3 | 6/2012 |

OTHER PUBLICATIONS

Breen, et al. Spine kinematics: a digital videofluoroscopic technique. Journal of Biomedical Engineering. 1989; 11: 224-8.

Breen, et al. Lumbar spine motion palpation compared with objective intervertebral motion analysis: preliminary findings. European Journal of Chiropractic. 2002; 50, 27-32.

Bryant. Method for determining vertebral body positions in the sagittal plane using skin markers. Spine 1989; 14(3): 258-65.

Carragee, et al. Low-pressure positive Discography in subjects asymptomatic of significant low back pain illness. Spine. 2006; 31(5): 505-509.

Cholewicki, et al. Method for measuring vertebral kinematics from videofluoroscopy. Clinical Biomechanics. 1991; 6: 73-8.

Cholewicki, et al. Lumbar posterior ligament involvement during extremely heavy lifts estimated from fluoroscopic measurements. Journal of Biomechanics. 1992; 25(1): 17-28.

Esses, et al. Kinematic evaluation of lumbar fusion techniques. Spine 1996; 21(6): 676-84.

Fujiwara, et al. The relationship between disc degeneration, facet joint osteoarthritis, and stability of the degenerative lumbar spine. Journal of Spinal Disorders. 2000; 13: 444-50.

Harada, et al. Cineradiographic motion analysis of normal lumbar spine during forward and backward flexion. Spine. 2000; 25: 1932-7;.

Johnsson, et al. Mobility of the lower lumbar spine after posterolateral fusion determined by roentgen stereophotogrammetric analysis. Spine. 1990. 15: 347-50.

Jones, M. D. Cervical spine cineradiography after traffic accidents. Archives of Surgery. 1962; 85: 974-81.

Kaigle, et al. Muscular and kinematic behavior of the lumbar spine during flexion-extension. Journal of Spinal Disorders. 1998; 11(2): 163-174.

Kleissen, Simultaneous Measurement of Surface EMG and Movements for Clinical Use, Medical & Biological Engineering, 27(3) pp. 291-97 (1989).

Kondracki, Digital Videofluoroscopy, Manual Therapy (1996) 1, 146-48.

Lariviere, et al. A triaxial dynamometer to monitor lateral bending and axial rotation moments during static trunk extension efforts. Clin Biomech (Bristol, Avon). Jan. 2001;16(1):80-3.

Lawrence, J. S. Disc degeneration. Its frequency and relationship to symptoms. Annals of Rheumatic Diseases. 1969; 28: 121-38.

Lee et al. Development and validation of a new technique for assessing lumbar spine motion. Spine. 2002; 27(8): E215-20.

McGregor et al. Spinal motion in lumbar degenerative disc disease. J one Joint Surg (Br). 1998; 80-B: 1009-1013.

Quick, et al. Real-Time MRI of Joint Movement with True FISP, J. Mag. Res. Imaging vol. 15(6), pp. 710-715 (2002).

Stokes, et al. Trunk muscular activation patterns and responses to transient force perturbation in persons with self-reported low back pain. Eur Spine J. 2006; 15:658-667.

Takayanagi, et al. Using cineradiography for continuous dynamic-motion analysis of the lumbar spine. Spine. 2001; 26(17): 1858-1865.

Teyhen, et al., A New Technique for Digital Fluoriscopic Video Assessment of Sagittal Plane Lumbar Spine Motion, Spine vol. 30(14), pp. E406-E413 (2005).

Waddell, G. The Back Pain Revolution. Churchill Livingstone. Edinburgh. 1998; Ch2 p. 23.

Wong, et al. Continuous dynamic spinal motion analysis. Spine. 2006; 31(4): 414-419.

Zheng, et al. Lumbar spine visualisation based on kinematic analysis from videofluoroscopic imaging. Medical Engineering and Physics. 2003; 25: 171-179.

Zheng, et al. Automatic Lumbar Vertebrae Segmentation in Fluoroscopic Images via Optimised Concurrent Hough Transform, 23rd Annual International Conf of IEEE Engineering in Med and Biology (2001).

\* cited by examiner

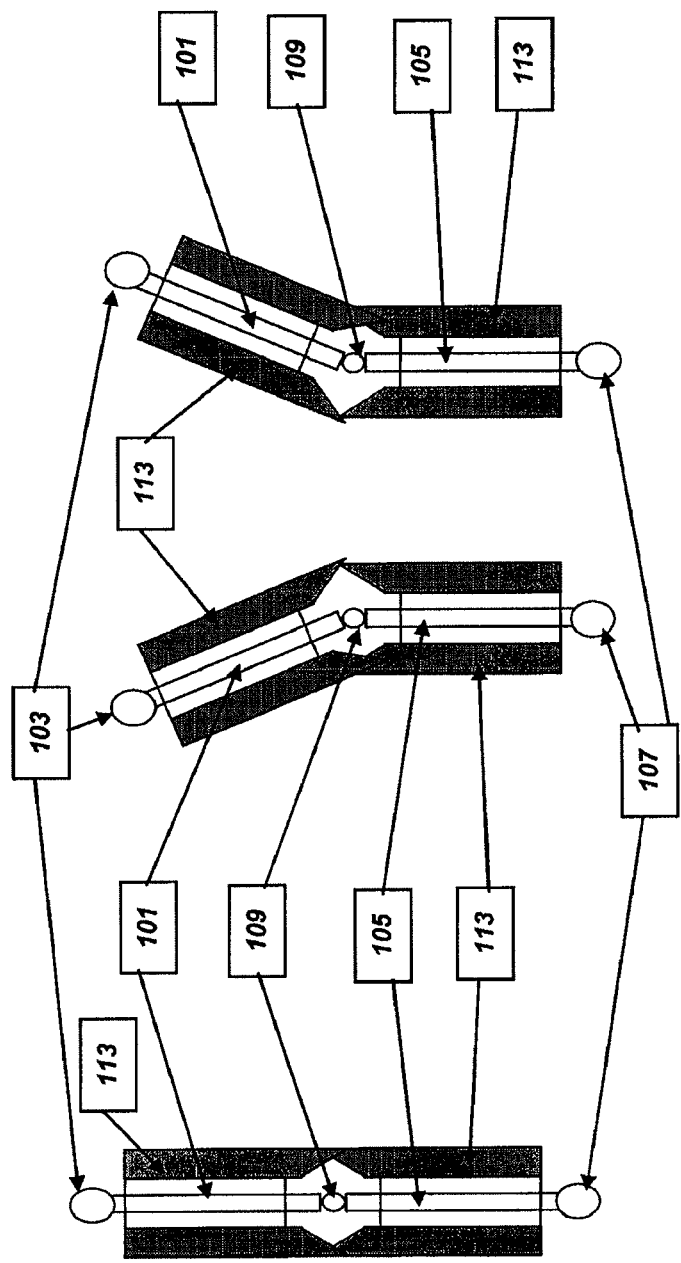

DEVICES, SYSTEMS, AND METHODS FOR MEASURING AND EVALUATING THE MOTION AND FUNCTION OF JOINTS AND ASSOCIATED MUSCLES

CROSS-REFERENCE

This application claims is a CONTINUATION of application Ser. No. 12/247,552 filed Oct. 8, 2008 now abandoned, entitled Devices, Systems and Methods for Measuring and Evaluating the Motion and Function of Joints, which claims the benefit of U.S. Provisional Application Nos. 60/978,907, filed Oct. 10, 2007, 60/981,922, filed Oct. 23, 2007, 61/015, 149, filed Dec. 19, 2007, and 61/054,426, filed May 19, 2008, which applications are incorporated herein by reference.

TECHNICAL FIELD

The present invention relates to devices, systems and methods for measuring and evaluating the motion and pathologies of a joint structure in a subject. The invention also enables a determination of whether, and to what extent, muscles associated with a joint are impacting the joint's biomechanics. The invention enables the biomechanics of a joint to be evaluated with a precision of less than 5°, preferably less than 3°, and even more preferably less than 1°. The enhanced biomechanical assessment facilitates orthopedic procedure and/or device suitability determination as well as orthopedic procedure and/or device evaluation.

BACKGROUND OF THE INVENTION

Health care providers rely on an understanding of joint anatomy and mechanics when evaluating a subject's suspected joint problem and/or biomechanical performance issue. Understanding anatomy and joint biomechanics assists in the diagnosis and evaluation of a subject for an orthopedic intervention. However, currently available diagnostic tools are limited in the level of detail and analysis that can be achieved. Typically, when treating joint problems, the intention is to address a specific structural or mechanical problem within the joint. For example, a surgeon might prescribe a specific procedure to correct the joint alignment problem, or a physical therapist might prescribe exercises to strengthen a specific tendon or muscle that is responsible for a joint problem, etc.

It follows, therefore, that the extent to which a specific treatable joint defect can be identified and optimally treated directly impacts the success of any treatment protocol. Currently available orthopedic diagnostic methods are capable of detecting a limited number of specific and treatable defects. These techniques include X-Rays, MRI, discography, and physical exams of the patient. These methods have become widely available and broadly adopted into the practice of treating joint problems and addressing joint performance issues. However, currently available diagnostic techniques provide measurement data that is imprecise and often inconclusive which results in an inability to detect many types of pathologies or to accurately assess pathologies that might be considered borderline. As a result, a significant number of patients having joint problems remain undiagnosed and untreated using current techniques, or worse are misdiagnosed and mistreated due to the poor clinical efficacy of these techniques.

There are currently no reliable techniques for identifying soft tissue injury. Muscle guarding is a well established concept that is hypothesized to be highly prevalent among sufferers of joint pain. In muscle guarding, a subject responds to chronic pain by immobilizing the painful area through involuntary muscle involvement. The ability to isolate different muscle groups is desirable to determine which muscle group or combination of groups, if any, could be contributing to, or responsible for, any joint dysfunction.

Additionally, the level of entrenchment of muscle guarding behavior cannot currently be determined. With respect to treatment decisions, the operative question in determining the level of "entrenchment" of any observed muscle guarding is to determine if the muscle guarding behavior is one which conservative methods of therapy could address through non-surgical therapy, or alternatively determining that the muscle guarding behavior so "entrenched" that such efforts would be futile and surgery should be considered.

Further, assuming that a system of measuring the surface motion of joints and the motion between internal joint structures that accounts for various types of muscle involvements would be possible, there would be a need for investigational data from controlled clinical trials to be collected across a broad population of subjects to afford for comparative analyses between subjects. Such a comparative analysis across a broad population of subjects would be necessary for the purpose of defining "normal" and "unhealthy" ranges of such measurements, which would in turn form the basis for the diagnostic interpretation of such measurements.

There have been significant technological innovations to the field of orthopedic interventions over the last few decades, specifically with the use of prosthetic and therapeutic devices to correct mechanical and structural defects of the bones and joints and to restore proper joint function. There have also been significant advances in the application of chiropractic and physical therapy approaches to correct muscle-, ligament-, and tendon-related defects. There has not however, been a corresponding improvement in the diagnostic methods used to identify proper candidates for these interventions. As a result, the potential impact and utility of the improvements in orthopedic intervention has been limited.

Imaging is the cornerstone of all modern orthopedic diagnostics. The vast majority of diagnostic performance innovations have focused on static images. Static images are a small number of images of a joint structure taken at different points in the joint's range of motion, with the subject remaining still in each position while the image is being captured. Static imaging studies have focused mainly on detecting structural changes to the bones and other internal joint structures. An example of the diagnostic application of static imaging studies is with the detection of spinal disc degeneration by the use of plain X-rays, and MR images. However, these applications yield poor diagnostic performance with an unacceptably high proportion of testing events yielding either inconclusive or false positive/false negative diagnostic results (Lawrence, J. S. (1969) Annals of Rheumatic Diseases 28: 121-37; Waddell, G. (1998) The Back Pain Revolution. Edinburgh, Churchill Livingstone Ch 2 p 22; Carragee et al. (2006) Spine 31(5): 505-509, McGregor et al. (1998) J Bone Joint Surg (Br) 80-B: 1009-1013; Fujiwara et al. (2000(a)) Journal of Spinal Disorders 13: 444-50).

Cine-radiography of uncontrolled weightbearing motion (Harada et al. (2000) Spine 25: 1932-7); Takavanagi et al. (2001) Spine 26(17): 1858-1865) has been used to provide a set of static images to which digital markers have been attached and transformed to give quantitative measurement of joint motion. Similar measurement of joint motion has been achieved using videofluoroscopy (Breen et al. (1989) Journal of Biomedical engineering 11: 224-8; Cholewicki et al. (1991) Clinical Biomechanics 6: 73-8; Breen et al. (1993)

European Journal of Physical Medicine and Rehabilitation 3(5): 182-90; Brydges et al. 1993). This method has also been used to study the effects on joint motion of weightlifting (Cholewicki et al. (1992) Journal of Biomechanics 25(1): 17-28). Prior procedures using this method involve using a manual process in which internal joint structures are marked by hand with digital landmarks on digital image files of consecutive frames of videoflouroscopy recordings of a subject's joint motion. A computer then automatically determines the frame-to-frame displacement between such digital landmarks to derive quantitative measurements of the motion of joint structures (Lee et al. (2002) Spine 27(8): E215-20). Even more recently, this approach has been accomplished using an automatic registration process (Wong et al. (2006) Spine 31(4): 414-19) that eliminates the manual marking process and thus reduces the laboriousness of the previous processes. However both of these methods, as well as all of the other methods mentioned in this paragraph, studied the motion of joints based on the imaging of uncontrolled, weightbearing body motion.

Using uncontrolled, weightbearing motion to derive quantitative measurements of joint motion confounds the diagnostic interpretation of such measurements so as to render them diagnostically useless. The diagnostic interpretation of such measurements would normally be based on a comparative analysis of joint motion measurements across a wide population of subjects, and would strive to identify statistically significant differences in these measurements between "normal" and "unhealthy" subjects, such that any given subject can be classified as "normal" or "unhealthy" based on that subject's joint motion measurement values. For such purposes, it is necessary to reduce the background variability of measurements across tested subjects as much as possible, so that any observed difference between "normal" and "unhealthy" subjects can be definitively attributable to a specific condition. Not controlling the motion that is being studied introduces variability into these comparative analyses due to differences that exist across testing subjects with respect to each subject's individual range of motion, symmetry of motion, and regularity of motion. These differences affect the joint motion of each subject differently, and collectively serve to create wide variability among joint motion measurements across subjects. Controlling for these factors by ensuring a consistent, regular, and symmetric body part motion during diagnostic testing serves to minimize the effects of these factors on a subject's relevant joint motion measurements, thereby reducing the variability of such measurements across subjects and therefore increasing the likelihood that such measurements will yield useful diagnostic results.

Purely qualitative methods for visualizing joint motion have been available for some time using cine-radiography (Jones, M. D. (1962) Archives of Surgery 85: 974-81). More recently, computer edge extraction of vertebral images from fluoroscopy has been used to improve this visualization for use in animations (Zheng et al. (2003) Medical Engineering and Physics 25: 171-179). These references do not, however, provide for any form of measurement or identification of objectively defined motion abnormalities, and therefore is of very limited diagnostic value other than in the detection of grossly and visibly obvious abnormalities that would be detectable using static image analysis methods. Without any quantitative or objective measurement parameters defined, it is impossible to utilize such approaches in comparative analyses across wide populations of subjects, which is required for the purpose of the producing definitive diagnostic interpretations of the results as being either "normal" or "unhealthy". Further, there have been no diagnostically useful validations of qualitative motion patterns that are generally absent in non-sufferers but present in subjects suffering from known and specific joint functional derangements or symptoms, or vice versa.

Prior attempts at controlling the motion to derive quantitative measurements have provided a more accurate measurement of joint motion, however, some aspects of the motion have continued to be uncontrolled. For example, while some researchers have been able to control the gross motion of the subject, they have not been able to control for the rotation of the patient at their hips while undergoing the controlled motion sweep. This uncontrolled rotation during the controlled sweep of trunk bending confounds the goal of controlling the motion, but also can confound the quantitative imaging results. When the subject rotates out of plane during the trunk bending, the definition of the vertebra in the image becomes compromised, making the vertebra harder to track throughout the image sequence, and thus confounding the diagnostic measurement results.

Methods with living subjects have been able to obtain a high degree of accuracy in measuring the motion of internal joint structures by placing internal markers on the bones of subjects and digitally marking sets of static images (Johnsson et al. (1990) Spine 15: 347-50), a technique known as roentgen stereophotogrammetry analysis (RSA). However RSA requires the surgical implantation of these markers into subjects' internal joint structures, requires the use of two radiographic units simultaneously, and requires a highly complicated calibration process for every single test, and therefore is too invasive and too cumbersome a process for practicable clinical application.

A method for determining vertebral body positions using skin markers was developed (Bryant (1989) Spine 14(3): 258-65) but could only measure joint motion at skin positions and could not measure the motion of structures within the joint. There have been many examples skin marker based spine motion measurement that have all been similarly flawed.

Methods have been developed to measure changes to the position of vertebrae under different loads in dead subjects, whose removed spines were fused and had markers inserted into the vertebrae (Esses et al. (1996) Spine 21(6): 676-84). The motion of these markers was then measured in the presence of different kinds of loads on the vertebrae. This method is, however, inherently impractical for clinical diagnostic use. Other methods with living subjects have been able to obtain a high degree of accuracy in measuring the motion of internal joint structures by placing internal markers on the bones of subjects and digitally marking sets of static images (Johnsson et al. (1990) Spine 15: 347-50), a technique known as roentgen stereophotogrammetry analysis (RSA). However RSA requires the surgical implantation of these markers into subjects' internal joint structures, requires the use of two radiographic units simultaneously, and requires a highly complicated calibration process for every single test, and therefore is too invasive and too cumbersome a process for practicable clinical application.

In addition to failing to control motion during testing, not accounting for the involvement and effects of muscles that are acting when a subject moves under their own muscular force while in a weight-bearing stance further adds to this variability by introducing such inherently variable factors such as the subject's muscle strength, level of pain, involuntary contraction of opposing muscle groups, and neuro-muscular co-ordination. Taken together, all of these sources of variability serve to confound diagnostic conclusions based on comparative analyses by making the ranges of "normal" and those of "abnormal" difficult to distinguish from one another other in a statistically significant way. Such an inability to distinguish between "normal" and "unhealthy" subjects based on a specific diagnostic measurement renders such a measurement diagnostically useless, as has been the case heretofore known which has focused on measurements of uncontrolled joint motion measured in subjects in weight-bearing postures and moving their joints through the power of their own muscles and in an uncontrolled fashion.

U.S. Pat. No. 5,505,208 to Toomin et al. developed a method for measuring muscle dysfunction by collecting muscle activity measurements using electrodes in a pattern across a subject's back while having the subject perform a series of poses where measurements are made at static periods within the movement. These electromyographical readings of "unhealthy" subjects were then compared to those of a "normal" population so as to be able to identify those subjects with abnormal readings, however does not provide for a method to report the results as a degree of departure from an ideal reading, instead can only say whether the reading is "abnormal". U.S. Pat. No. 6,280,395 to Appel et al. added an additional advantage to this method for determining muscle dysfunction by using the same method, yet adding the ability to better normalize the data by employing a more accurate reading of the thickness of the adipose tissue and other general characteristics that might introduce variability into the readings, as well as the ability to quantify how abnormal a subject's electromyographical reading is as compared to a "normal" population.

Electromyographic measurements taken during weight-bearing joint motion, with simultaneous recording of the motion of the body part using goniometers and also with simultaneous recordings of the motion of internal joint structures through the tracking of surgically-implanted metal markers, has been used to correlate muscle activity with the motion of joints and internal joint structures (Kaigle, supra). However this approach studied joint motion that was uncontrolled and required an invasive surgical procedure to place the metal markers, and thus were neither useful nor feasible for clinical diagnostic application.

Electromyography has also been used in conjunction with a device that provides transient force perturbation so as to observe whether there is a difference between subjects with low back pain and those without low back pain to determine how their muscles respond to such a force. (Stokes, Fox et al. 2006) The objective was to determine whether there is an altered muscle activation pattern when using a ramped effort. This approach however does not address the issue of which discrete muscle group or groups might account for the difference between activation patterns in subjects with joint dysfunctions and those without. Furthermore, this method does not take into consideration the internal structural joint motions and thus provides an incomplete set of information upon which to draw diagnostic conclusions.

What is therefore needed is an apparatus and process for using the apparatus that solves the previously-identified issues, thus providing the clinician and medical device researcher with valuable diagnostic data.

SUMMARY OF THE INVENTION

An aspect of the invention is directed to an apparatus adapted and configured to cause and control joint motion of a patient. An apparatus according to the invention comprises, for example, a first motion member configured to engage a patient proximal to a target joint; a second motion member configured to engage a patient distal to a target joint; and a coupling member configured to connect the first motion member to the second motion member and further adapted to allow rotation of the first and second motion member around an axis, wherein the apparatus is engageable with a medical diagnostic device and further configured to capture patient specific data. In some embodiments, the medical diagnostic device is, for example, an X-ray scanner, an X-ray tube with image intensifier tube, a magnetic resonance scanner, an infrared camera, a computed tomography scanner, an ultrasound scanner, an electromyography sensor unit, a digital camera and/or a camera. Furthermore, the medical diagnostic device can be configured such that it is detachably engaged to the apparatus controlling joint motion. In some set-ups, the medical diagnostic device is an electromyography sensor unit with sensors attached to the subject. In other embodiments, at least one sensor is provided for capturing patient specific data. In still other embodiments, a motion control device is provided. In yet other embodiments, a collimator, such as a dynamic collimator, is provided. In still other configurations, a motion controller is provided along with a collimator, and the collimator is moveable such that it can be adapted to differing geometries during a motion controlled by the motion controller. The apparatus can also be adaptable to engage a posture assistance device. Moreover, in some embodiments, the coupling member can be adaptable to allow translation. A motion controller can also be provided that is adapted to control a motion of the first and second motion member relative to the axis.

Another aspect of the invention is directed to a process for capturing data and controlling skeletal joint motion of a patient. The process comprises, for example, providing an apparatus adapted and configured to selectively cause and control joint motion of a patient having a first motion member configured to engage a patient proximal to a target joint; a second motion member configured to engage a patient distal to a target joint; and a coupling member configured to connect the first motion member to the second motion member and further adapted to allow rotation of the first and second motion member around an axis, wherein the apparatus is engageable with a medical diagnostic device further configured to capture patient specific data; positioning the patient in a position such that the target joint of the patient is at first position within a field of view; capturing, with a medical diagnostic device, a first diagnostic data from the patient and the apparatus; repositioning the apparatus such that the subject is placed in a second position different from the first position within the field of view; and capturing, with the medical diagnostic device, second diagnostic data from the patient and the apparatus in the second position. In some embodiments, the data capturing steps can further comprise use of a medical diagnostic device selected from the group consisting of X-ray scanner, X-ray tube with image intensifier tube, magnetic resonance scanner, infrared camera, computed tomography scanner, ultrasound scanner, electromyography sensor unit, digital camera and camera. Moreover, the data capturing steps can further comprise use of an electromyography sensor unit with sensors attached to the subject. Diagnostic data from the subject can be captured from at least one sensor. Furthermore, an additional step of administering a pharmaceutically active substance to the subject prior to capturing the first diagnostic data. In some embodiments of the method, the pharmaceutically active substance that is administered is an opioid substance, a muscle relaxant drug, such as baclofen, carisoprodol, chlorphenesin, chloroxazone, cyclobenzaprine, dantrolone, diazepam, metaxalone, methcarbamol and orphenadrine, or a non-opioid analgesic, such as fentanyl.

Yet another aspect of the invention is directed to a system for controlling motion of a target joint during a medical diagnostic procedure. The system comprises an apparatus adapted and configured to selectively cause and control joint motion of a patient having a first motion member configured to engage a patient proximal to a target joint; a second motion member configured to engage a patient distal to a target joint; and a coupling member configured to connect the first motion member to the second motion member and further adapted to allow rotation of the first and second motion member around an axis, wherein the apparatus is adapted and configured to engage a medical diagnostic device further configured to capture patient specific data; and of a medical diagnostic device selected from the group consisting of X-ray scanner, X-ray tube with image intensifier tube, magnetic resonance scanner, infrared camera, computed tomography scanner, ultrasound scanner, electromyography sensor unit, digital camera and camera, wherein the target joint can be maintained in a field of view by moving the medical diagnostic device, the apparatus, or a combination thereof.

Still another aspect of the invention is directed to an apparatus adapted and configured to cause and control joint motion of a patient comprising: a first motion member configured to engage a patient proximal to a target joint; a second motion member configured to engage a patient distal to a target joint and in moveable communication with the first motion member; and a collimator in communication with the first and second motions members to provide an indication of movement of the first motion member relative to the second motion member during motion of the joint, wherein the apparatus is engageable with a medical diagnostic device and further configured to capture patient specific data. In some embodiments, the medical diagnostic device is, for example, an X-ray scanner, an X-ray tube with image intensifier tube, a magnetic resonance scanner, an infrared camera, a computed tomography scanner, an ultrasound scanner, an electromyography sensor unit, a digital camera and/or a camera. Furthermore, the medical diagnostic device can be configured such that it is detachably engaged to the apparatus controlling joint motion. In some set-ups, the medical diagnostic device is an electromyography sensor unit with sensors attached to the subject. In other embodiments, at least one sensor is provided for capturing patient specific data. In still other embodiments, a motion control device is provided. In yet other embodiments, the collimator is a dynamic collimator. In still other configurations, a motion controller is provided, and the collimator is moveable such that it can be adapted to differing geometries during a motion controlled by the motion controller. In other embodiments, the apparatus is adaptable to engage a posture assistance device. Moreover, in some embodiments, the coupling member can be adaptable to allow translation. A motion controller can also be provided that is adapted to control a motion of the first and second motion member relative to the axis.

INCORPORATION BY REFERENCE

All publications, patents and patent applications mentioned in this specification are herein incorporated by reference to the same extent as if each individual publication, patent or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A-C illustrates the functionality of a collimator device

DETAILED DESCRIPTION OF THE INVENTION

I. Systems

Figure 1B:
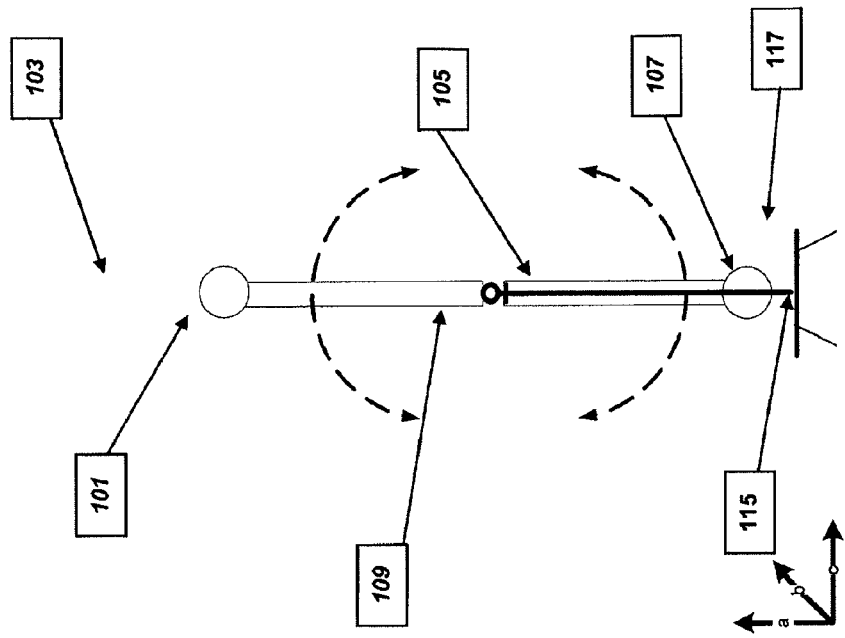
FIGS. 1A and 1B show front and side view block diagrams of the motion control device.
Figure 1A:
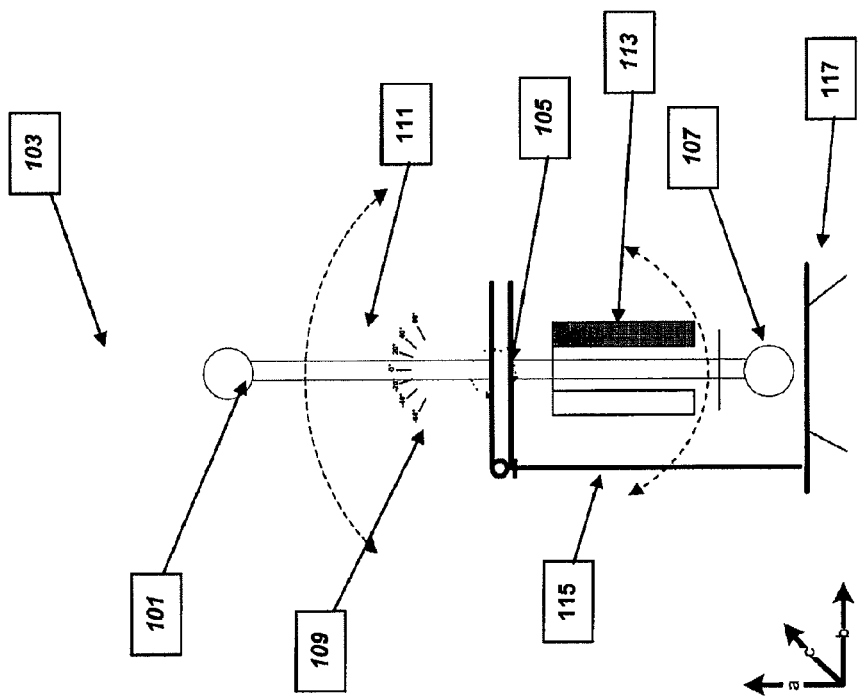

Turning now to FIG. 1, a motion control device is illustrated. An aspect of the invention is directed to an apparatus adapted and configured to cause and control joint motion of a patient and to determine the impact of muscle guarding on a non-weight bearing or weight-bearing joint. The apparatus includes a support frame base 117, which rests immovably on the floor or on a chair, table, or other posture assistance device by, for example, a high friction point of connection, and which provides the stability to bear the weight of the motion control device plus an attached patient in all of the device's operator-adjustable modes of operation.

The support frame vertical member 115 connects to the support frame base at a connection point that can be optionally rotatable around any axis relative to the support frame base 117, and lockable into a position relative to the support frame base 117 during device operation. This rotation of the support frame vertical member about the support frame base 117 can be optionally powered by an actuator placed between the support frame vertical member 115 and either the support frame base 115 or the support frame pivoting member 109. The support frame vertical member 115 and the connection between 117 incorporates the structural integrity while held in a locked position to bear the weight of the patient and the motion control device in all operation configurations.

The support frame pivoting member 109 connects to the support frame vertical member 115 and is selectively rotatable in any plane relative to the support frame pivoting member. The support frame pivoting member 109 is lockable into a position relative to the support frame vertical member 115 for operation. The rotation of the support frame pivoting member 109 can be optionally powered by, for example, an actuator connecting between the support frame pivoting member 109 and either the support frame base 117 or the support frame vertical member 115.

The support frame pivoting member 109 is composed of materials and is designed so as to not interfere with the field of imaging, which it completely or partially occupies during imaging. In the case of X-ray based imaging, this requires that the material occupying the field of imaging be radio-lucent, and in the case of MRI imaging this requires that metallic materials are avoided so as to avoid the disruptive artifacts these materials can cause on MR images.

The support frame pivoting member 109 also connects with both the attachment arms 101 and 105, such that both attachment arms 101 and 105 are independently and optionally rotatable in any axes relative to the support frame pivoting member 109. This independent rotation of 101 and 105 about any axes relative to the support frame pivoting member 109 can be optionally powered by a pair of actuators, each connecting on one end to one of the attachment arms 101 and 105 and on the other end to either the support frame pivoting member 109, the support frame base 117, or the support frame vertical member 115. After independently rotating the attachment arms 101 and 105 about axes relative to the support frame pivoting member 109 so that the attachment arms 101 and 105 are in the prescribed configuration for testing, the support frame pivoting member then allows the attachment arms 101 and 105 to lock into a position relative to the support frame pivoting member 109.

After locking into their positions for operation, the attachment arms 101 and 105 are then independently and optionally configurable to move through a sweep of motion during testing with a medical diagnostic device. In some cases, only one of the attachment arms 101 and 105 will be configured to move during testing, but in other cases both attachment arms can be configured to move during testing. The support frame pivoting member allows the operator to configure the exact sweep of motion for each attachment arm 101 and 105, which includes the ability to set some or all of the following motion parameters independently for the attachment arm or arms that are set to move during diagnostic testing: (1) the plane of motion in the case that planar non-rotational motion is desired; (2) the location and orientation of the axis of rotation in the case that rotational motion is desired; (3) the non-planar trajectory of motion in the case that non-planar, non-rotational motion is desired, (4) the beginning point of motion and the end point of motion in the case that these parameters are pre-defined; (5) whether or not a force will be applied to the attachment arm or arms to provide for passive joint motion on the part of the patient by, for example, actuators placed between each of the attachment arms 101 or 105 and either the support frame base 117, the support frame vertical member 115, or the support frame pivoting member 109 on the other ends; and (6) if there is to be an applied force acting on either of the attachment arms 101 and 105 then the velocity and applied force at each point in the sweep of tested motion. In one design of the motion control device, the motion of the attachment arms 101 and 105 is guided by a mechanical guide interposed between the attachment arms 101 and 105 and the support frame pivoting member 109, the support frame base 117, or the support frame vertical member 115. The motion of the attachment arms 101 and 105 can be optionally configured to: (1) allow for active bending of the joint to the subject's maximum voluntary bending angle, (2) active bending of the joint to a predetermined bending angle, (3) passive bending o the joint to any number of predetermined bending angles. If there is to be an applied force acting on either of the attachment arms 101 and 105, then the magnitude of said force produced by the actuator can be controlled by an electronic controller that can optionally produce forces based on: (1) predetermined force levels, (2) data provided by other actuators or sensors within the motion control device during testing, or (3) data provided by other devices, such as the imaging equipment or posture assistance device during testing.

The attachment arms 101 and 105 each further comprise a support panel on which a patient's body part can rest and attachment mechanisms 103 and 107 that secure either a patient's body part or a posture assistance device to either of the attachment arms 101 and 105. In some instances when the attachment mechanisms 103 and 107 are the only connection point between the patient and the motion control device, each attachment mechanism can additionally function as a support mechanism in bearing some or all of the weight of the attached body part at rest or in motion.

In the case that either attachment mechanism 103 and/or 107 is configured to attach to a patient, then either attachment mechanism 103 and/or 107 can be a strap, tie, sling, boot, helmet, glove, or any type of device that will attach to the patient's body part that connects to the joint of interest. The attachment mechanisms 103 and/or 107 are attached to the attachment arms 101 and 105 by a mechanism that is selectively movable or immovable, as set by the operator. In the case that the mechanism(s) that attaches the attachment mechanisms 103 and/or 107 to the attachment arms 101 and 105 is (are) configured to be movable, this mechanism will allow the attachment mechanisms 103 and/or 107 to freely rotate and/or translate relative to the attachment arms 101 and 105. The location, size, length and geometry of the attachment arms 101 and 105 and the location, size, and geometry of the attachment mechanism 103 and/or 107 can be configured to sufficiently support and position the patient's body part to afford for physiological function of the joint of interest. In the case when either attachment mechanisms 103 and/or 107 connects directly to a posture assistance device such as a table, chair, or other type of posture assistance device, then the attachment can be an adjustable tie, strap, bolt, clamp, pin, or any other type of device that can be removably connected to a posture assistance device so that the posture assistance device and the motion control device are immovably connected and function as a single integrated patient handling device. Thus with respect to the attachment mechanisms 103 and 107, these mechanism have three principal operational modes: (1) both attachment mechanisms 103 and 107 connect to the patient, (2) attachment mechanism 103 connects to a patient while attachment mechanism 107 connect to a posture assistance device, and (3) attachment mechanism 107 connects to a patient while attachment mechanism 103 connect to a posture assistance device. In an alternative embodiment, one of the attachment arms 101, or 105, is effectively non-existent, and the attachment mechanism 103 or 107 has the functionality to connect to the posture assistance device and act as the pivot point of the apparatus.

Data encoding devices 111 can be optionally attached to either of the attachment arms 101 and 105 or the attachment mechanisms 103, 107 and enables data to be transmitted directly to the medical images or other diagnostic formats. During operation of the device, there are several sets of data that can be generated by the operation of the motion control device or by the operation of other devices used during testing, such as a posture assistance device or the medical diagnostic device. Such data could include: time synchronization data which is data indicating the exact point in time when the motion device begins and ends a tested motion sequence; the position of each or both of the attachment arms 101 and/or 105, which could be a goniometer measurement, a protractor measurement, or a measurement of the displacement of each attachment arm relative to the starting position; parameters associated with the actuators, such as the level of applied force, displacement, velocity, or other parameters; the weight applied to the attachment arms 101 and 105 by the patient at any given moment; the force applied by the subject on the attachment arms 101 and 105 at any given moment; the weight of the subject bearing down on all or part(s) of the posture assistance device; or any other measurement parameter that is relevant to the tested motion and that can be generated by, for example, sensors included within the motion control device or by an input from a data source external to the motion control device, such as the posture assistance device or the medical diagnostic device. The data encoding devices 111 are either mechanical or digital devices that are capable of producing discernable analog or digital markings within the field of imaging that therefore get captured on the medical images resulting from the operation of the present invention (when the medical diagnostic device is a medical imaging device) that: (1) do not interfere with part of the field of imaging of interest for the prescribed diagnostic study, (2) can transmit data via the image that can be decoded at a later point in time such that all encoded data can be derived entirely through an analysis of each medical image. In one embodiment of the present invention using X-ray based fluoroscopy imaging, the data encoding devices 111 can be a radio-opaque protractor showing the angular displacement of an attachment arm 101 and/or 105, or alternatively could be a radio-opaque analogue needle-gauge to measure the current through the actuator at any point in time.

A collimator device 113 may be optionally attached to either or both of the attachment arms 101 and/or 105 for use in the case of ionizing radiation based imaging modalities. This collimator device is intended to block the path of ionizing radiation for one or both of two purposes: (1) minimize the dose of absorbed radiation on the part of the patient, and (2) minimize "flare", which can degrade the contrast of medical images and can occur when X-rays pass unimpeded from the source to the detector without first passing through the patient. This collimator device is composed of a leaded material or some other material with sufficient density as to partially or completely block ionizing radiation from passing through it. Stationary collimator devices that do not adjust during imaging are not useful, as the field of interest within the imaging frame changes as the joint of interest is in operation during testing. Therefore the collimator device 113 is intended to maintain a changing field of interest within the imaging frame as the position of the patient's anatomy changes as a function of normal joint operation, such that "flare" and radiation dose to the patient are both minimized while not obscuring any of the physiologic structures of interest. In one embodiment, the collimator connects to both attachment arms 101 and 105 according to FIG. 2 so that only specific band around each attachment arm is imaged. For situations in which it is feasible, it is ideal to place the collimator between the patient and the radiation source so as to block radiation that would have imaged parts of the patient's anatomy that are not of interest for the prescribed diagnostic study. The collimator device 113 may also incorporate an actuator that is intended to change the position and geometry of the shielding pieces dynamically during the tested motion. This actuator can be controlled by an electronic control system that incorporates stored input data or real time input data, both data coming from other parts of the motion control device or from another device such as an imaging device or a posture assistance device. The purpose of this functionality of the collimator device is to capable of dynamically adjusting the geometry of the shield during tested motion so as to maximize the benefit of the collimator device in terms of reducing radiation dose to the patient or in terms of reducing "flare", or both.

Furthermore the apparatus can be adapted and configured to engage a medical diagnostic device configured to capture data on the subject. Medical diagnostic devices typically include, for example, any device having a sensor adapted and configured to capture data from the subject (patient). For example, X-ray scanners, X-ray tubes with image intensifier tube, magnetic resonance scanners, infrared cameras, computed tomography scanners, ultrasound scanners, electromyography sensor units, digital camera and cameras, and electromyography sensor unit with sensors attached to the subject. The apparatus can be adapted and configured such that the medical diagnostic device detachably connects to the apparatus.

The apparatus can further be adapted and configured to keep a specific part of the patient's anatomy within the imaging field of interest during imaging. This can be accomplished by an imaging field adjustment mechanism capable of calculating the positional adjustments necessary to keep the joint of interest within and/or centered within the imaging field, then producing a movement between the support frame base 117 and the support frame vertical member 115, such that the specific part of the patient's anatomy is held within and/or centered within the field of imaging. In one embodiment, this imaging field adjustment mechanism would function as follows: (1) while attached to the apparatus, the patient is moved to extreme position #1 of the motion sweep that is being studied; (2) the apparatus is positioned relative to the medical diagnostic device such that the anatomy of interest on the patient is centered in the field of image of the diagnostic device; (3) this relative position between the imaging device and the apparatus is recorded as extreme position #1; (4) the patient is then moved to extreme position #2 of the motion sweep that is being studied; (5) this relative position between the imaging device and the apparatus is recorded as extreme position #2. Once these two extreme relative positions between the apparatus and medical diagnostic device have been recorded, the imaging field adjustment mechanism then affects a relative motion between the support frame base 117 and the support frame vertical member 115 from extreme position #1 to extreme position #2, and possibly back again, in such a way that this relative motion is synchronized with the motion sweep of the apparatus to hold a specific part of the patient's anatomy within and/or centered within the imaging field of interest. Furthermore, the calculation of motion between the support frame base 117 and the support frame vertical member 115 required to keep the anatomy of interest within the imaging field can be recorded and integrated into the computation of the range of motion of the specific joint of interest. In an alternative embodiment of the imaging field adjustment mechanism, an image centering marker is placed on the patient that denotes where the center of the imaging field should be positioned. The image centering marker interacts with the medical diagnostic device in such a way that the center of the imaging field always remains fixed on the image centering marker. So as to not interfere with the anatomy of interest, the image centering marker does not have to be in the actual center of the imaging field, but instead in a position within the image that remains relatively fixed throughout the motion. Data encoding devices can be optionally attached to either of the attachment arms 101 and 105 and/or the patient and data to be transmitted directly to the medical images or other diagnostic formats. During operation of the device, there are several sets of data that can be generated by the operation of the motion control device or by the operation of other devices used during testing, such as the attachment mechanisms 103 and 107, or the medical diagnostic device. Such data could include: time synchronization data which is data indicating the exact point in time when the motion device begins and ends a tested motion sequence; the position of each or both of the attachment arms 101 and 105, which could be a goniometer measurement, a protractor measurement, or a measurement of the displacement of each attachment arms 101 and 105 relative to the starting position or relative to the attachment mechanisms 103 and 107; parameters associated with the actuators, such as the level of applied force, displacement, velocity, or other parameters; the weight applied to the attachment arms 101 and 105 by the patient at any given moment; the force applied by the subject on the attachment arms 101 and 105 at any given moment; the displacement, velocity, or other parameters associated with the imaging field adjustment mechanism, or any other measurement parameter that is relevant to the tested motion and that can be generated by, for example, sensors included within the motion control device or by an input from a data source external to the motion control device, such as the medical diagnostic device. The data encoding device may either be mechanical or digital devices that are capable of producing discernable analog or digital markings within the field of imaging that therefore get captured on the medical images resulting from the operation of the present invention (when the medical diagnostic device is a medical imaging device) that: (1) do not interfere with part of the field of imaging of interest for the prescribed diagnostic study, (2) can transmit data via the image that can be decoded at a later point in time such that all encoded data can be derived entirely through an analysis of each medical image. In one embodiment of the present invention using X-ray based fluoroscopy imaging, the data encoding device can be a radio-opaque protractor showing the angular displacement of the attachment arms 101 and 105, or alternatively could be a radio-opaque analogue needle-gauge to measure the current through the actuator at any point in time.

A variety of configurations of the apparatus or devices of the invention are also contemplated. For example, in one embodiment of the invention the pivoting member 109, the attachment arms 101 and 105, and the attachment mechanisms 103 and 107 function together as an assembly that is detachable from the support frame base 117 and the support frame vertical member 115. In such an embodiment, neither the support frame base 117 nor the support frame vertical member 115 are included in the apparatus. Other apparatuses would be appreciated by those skilled in the art. See, for example, U.S. Patent Publication US 2005/0259794 A1 to Breen for Method for Imaging the Relative Motion of Skeletal Segments discloses an apparatus for the measurement of skeletal joint motion in a subject which comprises a passive motion machine. U.S. Patent Publication US 2007/0287900 A1 to Breen and Deitz for Devices, Systems and Methods for Measuring and Evaluating the Motion and Functionality of Joint Structures and Associated Muscles, Determining Suitability for Orthopedic Intervention, and Evaluating Efficacy of Orthopedic Intervention discloses devices, systems and methods for measuring and evaluating the motion and pathologies of a target joint structure in a subject.

The apparatus can be configured such that a first plane of either attachment arm 101 and 105 is in one of a horizontal plane or a vertical plane. The device attachment arm 105 can be configured such that it is actuated by a user. The diagnostic device can be connected to the either or both attachment arm 101 and 105 in some embodiments. Additionally, the attachment arms 101 and 105 can function as a support frame. The attachment arms 101 and 105 in the apparatus can further be adapted and configured to move automatically, semi-automatically, or manually.

According to the present invention there is provided the specification of a methodology for interpreting the measurements provided by the present invention to generate diagnostic results that can be clinically applied for the treatment of subjects with joint problems or performance issues

II. Device Operation

FIG. 2 illustrates one embodiment of the motion control device wherein the collimator device 113 is attached. FIG. 2A shows the collimator device 113 with the motion control device in a neutral position. FIGS. 2B and 2C show how the collimator does not obscure the joint region of interest within the imaging frame when the attachment arms 101 and 105 are positioned at an angle relative to each other.

Figure 3:
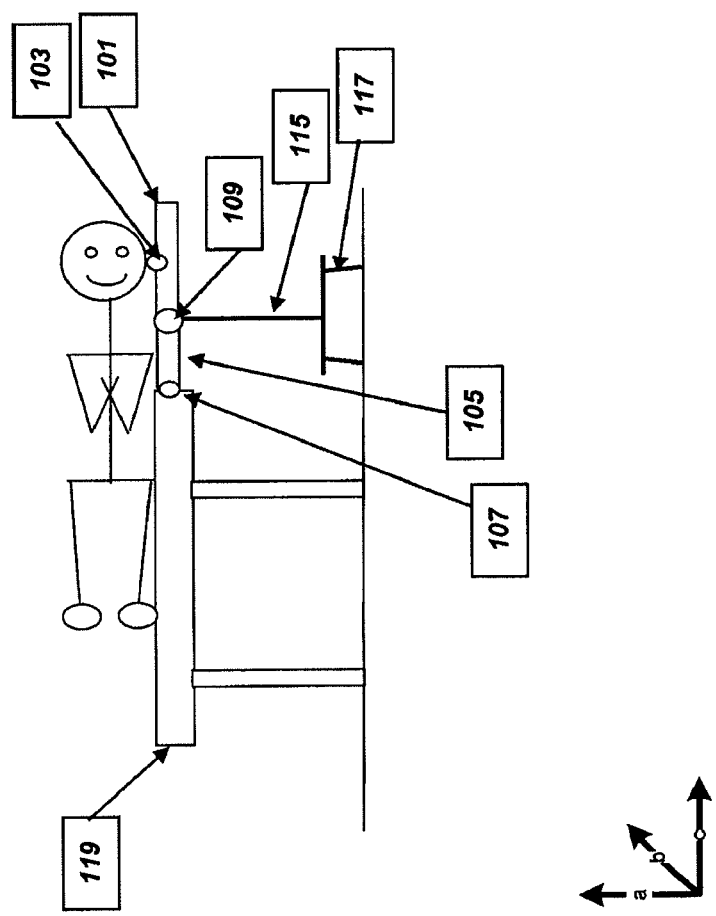
FIG. 3 illustrates a device used in conjunction with a patient examination table

FIG. 3 illustrates one use of the motion control device when used in combination with a posture assistance device 119. In this example, the posture assistance device 119 is a patient examination table. In this configuration, the attachment arm 101 will rotate within the b-c plane.

Figure 4:
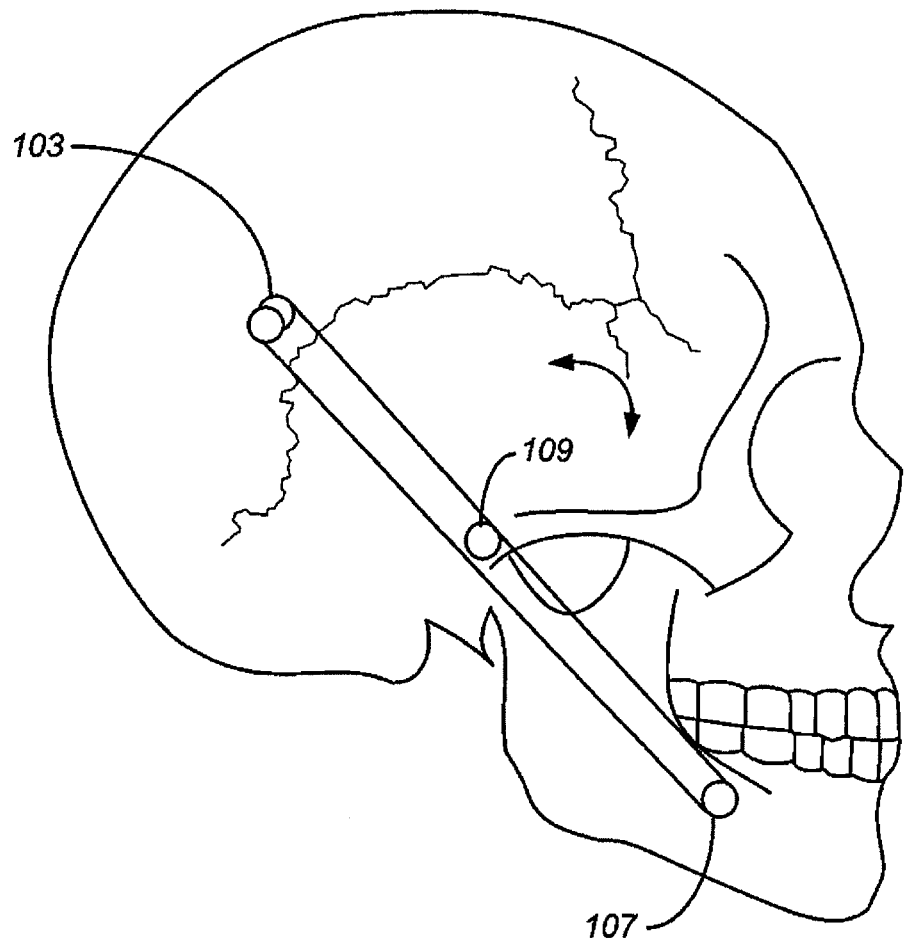
FIG. 4 illustrates a device used in conjunction with the jaw.

FIG. 4 illustrates a device used in conjunction with the jaw. The device is secured to the patient such that the joint is positioned adjacent to the patient's target joint, e.g., jaw joint. Securement can be achieved by any suitable method including the use of straps or a helmet. The patient then engages in motion which employs the joint and images are taken. Additionally, images can be taken of the joint in operation without the device in order to determine the impact of muscle guarding engaged in by the patient on the joint. The results of the two images studies can then be compared.

Figure 5:
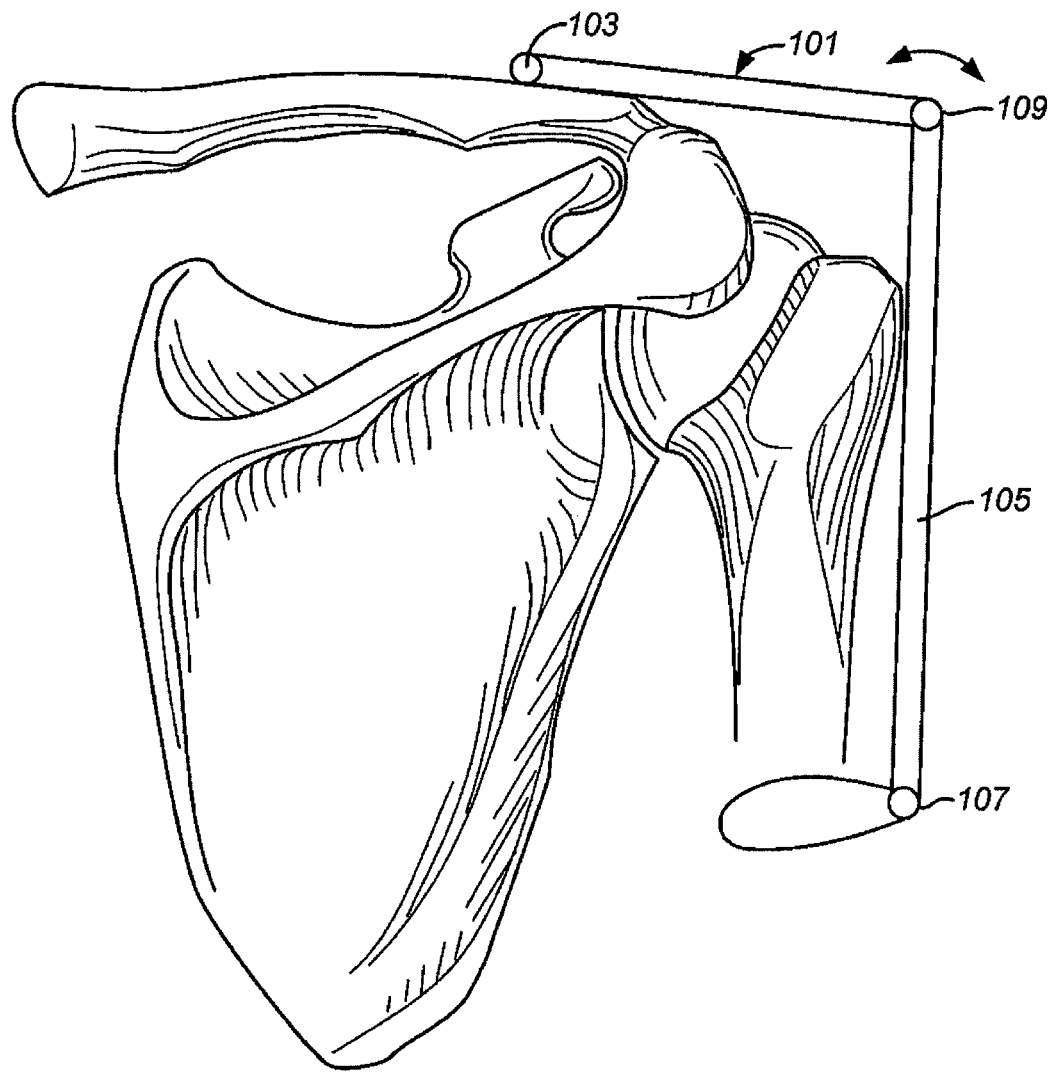
FIG. 5 illustrates a device used in conjunction with the shoulder.

FIG. 5 illustrates a device used in conjunction with the shoulder. The device is secured to the patient such that the joint is positioned adjacent to the patient's target joint, e.g., shoulder joint. Securement can be achieved by any suitable method including the use of straps, harness, or sling. The patient then engages in motion which employs the joint and images are taken. Additionally, as described above images can be taken of the joint in operation without the device in order to determine the impact of muscle guarding engaged in by the patient on the joint. The results of the two images studies can then be compared.

Figure 6:
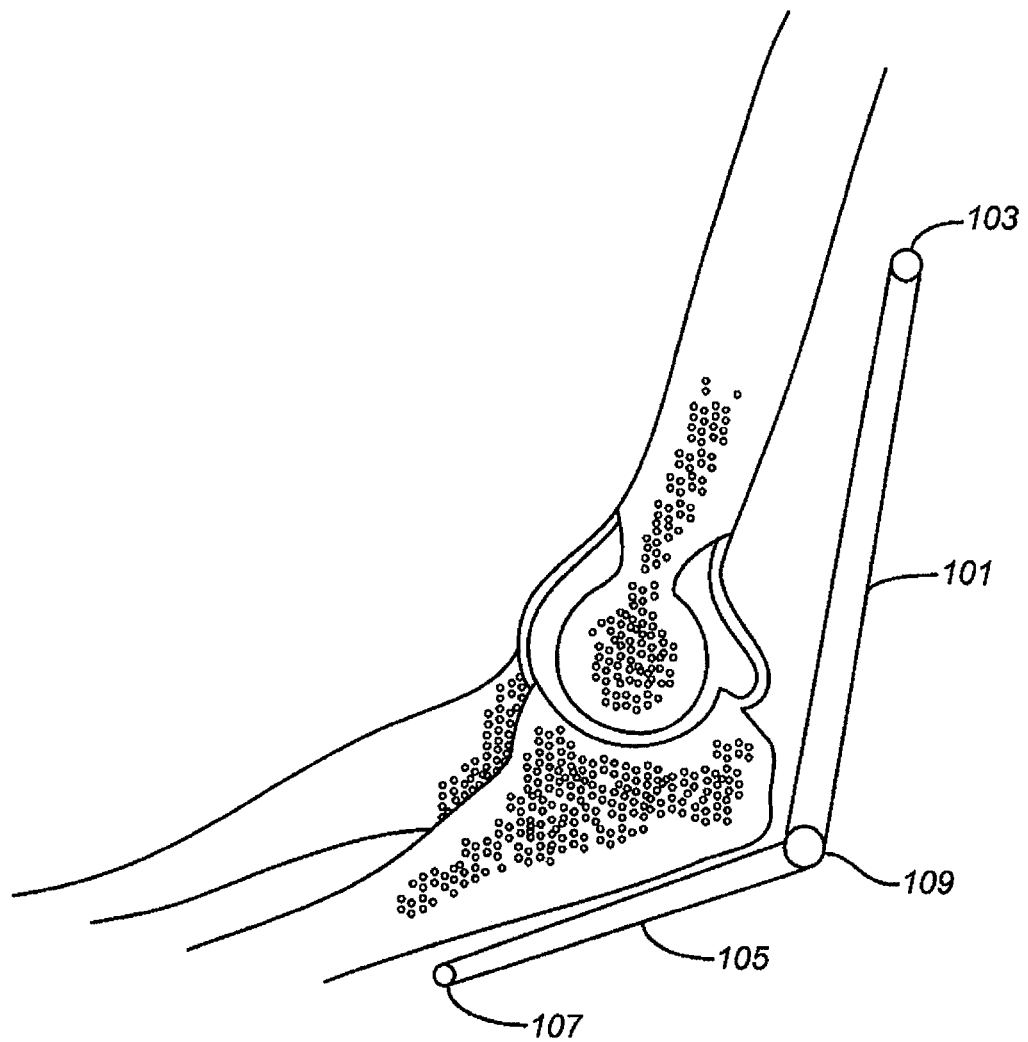
FIG. 6 illustrates a device used in conjunction with an elbow.

FIG. 6 illustrates a device used in conjunction with an elbow. The device is secured to the patient such that the joint is positioned adjacent to the patient's target joint, e.g., elbow joint. Securement can be achieved by any suitable method including the use of straps, harness, or sling. The patient then engages in motion which employs the joint and images are taken. Additionally, as described above images can be taken of the joint in operation without the device in order to determine the impact of muscle guarding engaged in by the patient on the joint. The results of the two images studies can then be compared.

Figure 7:
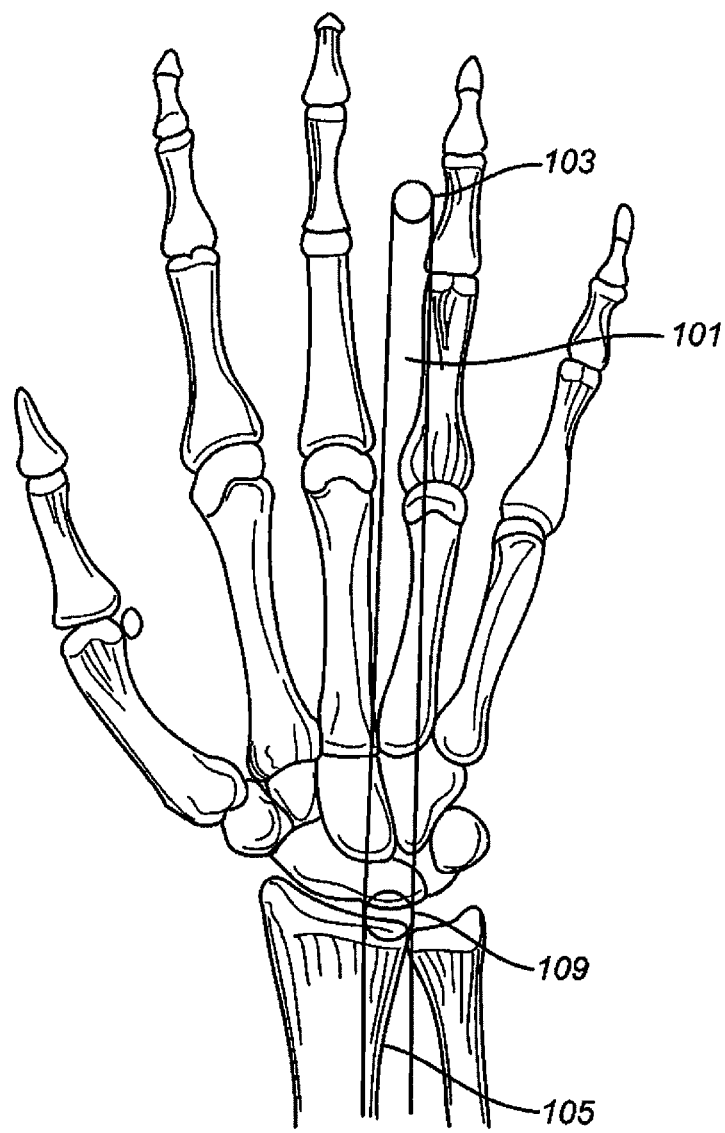
FIG. 7 illustrates a device used in conjunction with a wrist.

FIG. 7 illustrates a device used in conjunction with a wrist. The device is secured to the patient such that the joint is positioned adjacent to the patient's target joint, e.g., wrist joint. Securement can be achieved by any suitable method including the use of straps, harness, or sling. The patient then engages in motion which employs the joint and images are taken. Additionally, as described above images can be taken of the joint in operation without the device in order to determine the impact of muscle guarding engaged in by the patient on the joint. The results of the two images studies can then be compared.

Figure 8A:
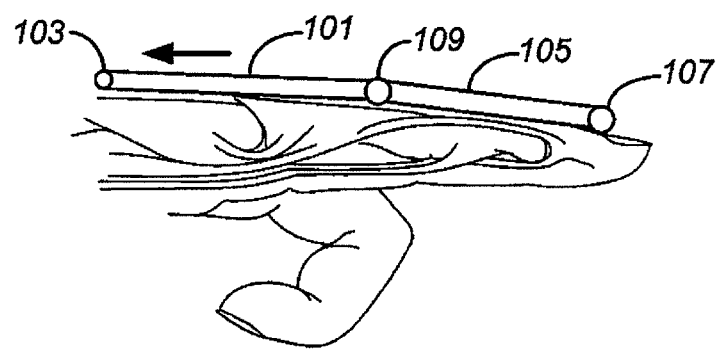
FIGS. 8A-B illustrate a device used in conjunction with a finger.
Figure 8B:
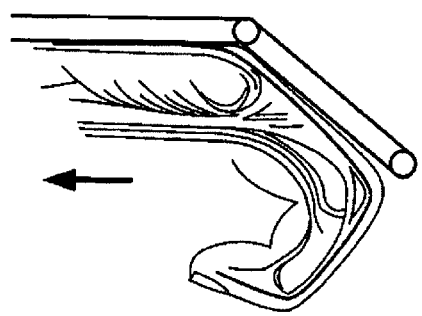
Figure 9:
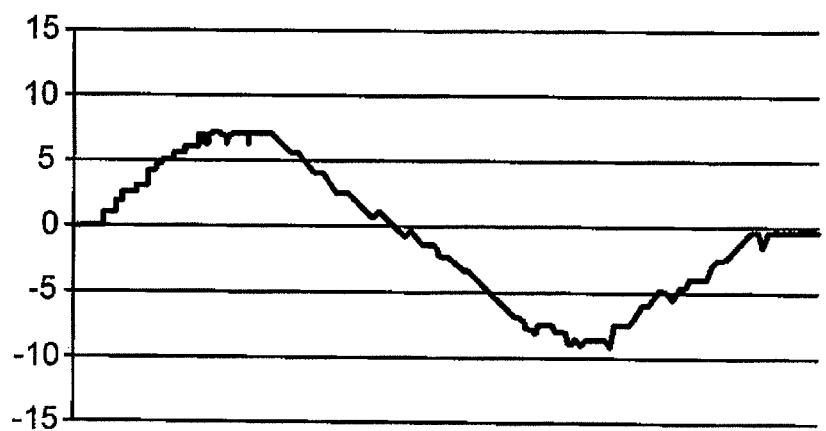
FIG. 9 illustrates a hypothetical range of motion where a plurality if images being sampled during the continuous motion which achieves an output having minimal noise.

FIGS. 8A-B illustrate a device used in conjunction with a finger, the device is secured to the patient such that the joint is positioned adjacent to the patient's target joint, e.g., finger joint. Securement can be achieved by any suitable method including the use of straps, harness, sling, or glove. The patient then engages in motion which employs the joint and images are taken. Additionally, as described above images can be taken of the joint in operation without the device in order to determine the impact of muscle guarding engaged in by the patient on the joint. The results of the two images studies can then be compared.

Ability to Provide Unguided Motion:

The devices can provide guided motion in the form of imposing a rotation about a fixed axis and within a specific plane of motion. In some instances it would be possible to provide guided motion in the form of imposing a rotation; however, instead of the rotation being about a fixed axis, the axis of rotation would be free floating. In such a case, the center of rotation is not fixed about an axis, but instead determined by the subject's internal joint mechanics. In other instances it would be possible to provide for unguided motion of the joint, wherein the subject's internal joint mechanics provide the guidance for the joint motion, as opposed to having the guidance imposed on the subject by the motion control devices.

Ability to Incorporate Body Positioning Tools:

The devices can incorporate the use of positioning tools or attachments so as to change the natural configuration of the joint being considered. As an example, a positioning tool could be placed under a subjects legs so as to change the angle of the spinal column before undergoing joint motion analysis.

Different Orientations of the Patient Attachment Arm with Respect to the Support Device Attachment Arm:

The devices provide a capability to hinge the motion of the patient attachment arm with respect to the support device attachment arm, however these two components are restricted from twisting along the longitudinal axis with respect to one another. Both latitudinal hinging and longitudinal twisting may also be provided between these components.

Different Orientations of the Diagnostic Imaging System:

The present invention contemplates a mechanism adapted and configured to perform diagnostic imaging of a joint where the field of imaging is fixed in space; however a diagnostic imaging system that does not have a field of imaging that is fixed in space could also be utilized. In such a case, the diagnostic imaging equipment would be operably moveable so that the field of imaging does not stay fixed in space, but instead would stay fixed with respect to: (1) the motion platform, (2) a landmark on the subject, or (3) any trajectory defined by the operator.

Other Diagnostic Imaging Systems:

The present invention contemplates a compatibility with all types of diagnostic imaging that are capable of producing moving images of joint motion. The method typically utilizes videoflouroscopy technology, CT scans, and magnetic resonance imaging. However, other diagnostic imaging methods such as ultrasound imaging, and imaging methods not yet invented could also be utilized. In addition, three-dimensional imaging platforms could be employed if the motion control devices had the capability to move along a three dimensional surface, as opposed to within a two dimensional plane, as is contemplated in the preferred embodiment of the motion control device. One skilled in the art will appreciate that as additional medical scanning or diagnostic devices become available, the present invention can be adapted to accommodate them.

Other Muscle Involvement Diagnostic Systems:

The present invention contemplates the use of surface electromyography for the measurement of muscle involvement, however other diagnostic systems may be used as well in an alternative embodiment such as MRI and ultrasound or other technologies not yet invented. These other diagnostic systems may or may not be sensor based. One skilled in the art will appreciate that as additional medical scanning or diagnostic devices become available, the present invention can be adapted to accommodate them.

Other Interpretation Methodologies Other than Those Listed:

methodologies for interpreting the measurements are provided by the present invention to generate diagnostic results that can be clinically applied in the treatment of subjects with joint problems or performance issues. While these aspects are necessary for reducing to practice the diagnostic apparatus and methods given in the first, second and third aspects of the invention, these aspects may be alternatively embodied by other interpretation methodologies that can be applied to the diagnostic measurements afforded by the apparatus and method of the present invention. These might include applications of the diagnostic measurements outside of the boundaries of validation that are provided for through controlled clinical trials using the diagnostic apparatus and method. These might also include less structured interpretation methodologies, and methodologies applied by practitioners other than therapists, physicians, surgeons, chiropractors, veterinarians, and other health professionals.

Diagnostic Use of Other Drugs:

The present invention contemplates the optional diagnostic use of muscle relaxant drugs such as metaxalone or diazepam, systemic pain drugs such as oral opioid drugs, and/or local pain drugs such as transdermal lidocaine. In an alternative embodiment of the invention, different drugs other than those listed in the preferred embodiment might be shown to demonstrate a diagnostically useful result, and therefore might become a part of the operation of the present invention.

Exclusion of Measurements that are Proven to not be Important:

Certain measurements contemplated in the preferred embodiment have not yet been validated as providing any diagnostic value. For example, measuring electromyography might be shown not to be necessary to perform during every testing event. This could happen if electromyography readings are shown to be negligible. Alternative embodiments of the apparatus could exclude certain measurements in certain configurations if such measurements are demonstrated to be measurable by proxy, or to be of very limited clinical and/or diagnostic value.

The Measurement of Other Joint Motion Parameters not Contemplated in the Preferred Embodiment:

The joint motion parameters that determine the apparatus configurations contemplated in this application are those that can be described as being: (1) weight-bearing or non-weight-bearing, (2) with or without the involvement and measurement of external forces, (3) involving or not involving pain-associated muscle involvement, and (4) involving or not involving systemic reductions in overall muscle activity. The preferred embodiment of the diagnostic method of the present invention will involve not only the configurations to accommodate the above-mentioned motion parameters, but also will possibly contemplate other motion parameters not listed above.

III. Evaluation Techniques

The methodology specified below puts forward a proposed method to utilize the present invention to assess the extent of dysfunctionality of specific muscles that could be suspected of causing joint pain or performance problems. The process listed below can be applied to any joint in humans and animals with internal bony skeletons, and should be applied to any given joint in any given type of organism before conclusive diagnostic results regarding that joint in that organism can be derived from measurements based on the present invention. According to the present invention there is provided the specification of a methodology for utilizing all or any one of the device in a diagnostic measurement process that also involves the collection of surface electromyography (sEMG) measurement signals taken from sEMG sensor electrodes that are placed on the subjects body prior to the initiation of this diagnostic measurement process. The measurements provided by the present invention can be used to derive quantitative assessments of the "dysfunctionality" of muscles that attach to and are proximal to the internal joint structures of interest. This information can be used diagnostically either with or without the additional measurements of joint surface motion and measurements of the motion of internal joint structures. The below listed process contemplates the use of the device.

The process that could be employed is:

a. For any given joint, assessing the involvement of muscles during joint motion for the purpose of detecting muscle dysfunction by using the device in conjunction with sEMG either before, during, or after acquiring images with the imaging device.

b. Begin by recording the joint muscle activity and by attaching sEMG electrodes to the subject in near proximity to the joint that is being investigated and by using a standardized protocol to ensure consistent placement across subjects, and by attaching the subject to the device as described above. Instruct the subject to actively move the target joint to a maximum voluntary angle in the absence any powered assistance or resistance coming from the device. For these motions, the external force system is disengaged and the movement angle data from the device is synchronously recorded with the sEMG signals that are measured during the movement. Parameterize the sEMG signals from this motion sequence into a single number or index, and this parameterized variable is referred to as $EMG_{Active, WB}$.

c. Have the subject return to the joint neutral position then engage the external force system to produce a known and measured resistive force acting in the direction opposite the movement and also acting against the subjects own motive muscle forces for the purpose of providing a resistive load against the subject's movement. Instruct the subject to move against the load such that the load is overcome and the subject can initiate the movement. Instruct the subject to stop moving at the midway point through the joint movement, and to hold this position such that the subject's muscular forces are in isometric opposition to the resistive load forces transmitted by the device. Record the sEMG signals and the magnitude of the resistive load while the subject holds this posture.

d. Use the known force parameter as well as a parameterization of the recorded sEMG signal from the above step to calculate a force/sEMG scaling parameter that can be used to correlate any parameterized sEMG measurement to a specific force parameter for any sEMG measurement from any given subject. Use this scaling parameter to express all parameterized sEMG measurements in terms of the muscular forces that they are associated with. This scaling parameter is referred to as $SF_{EMG\text{-}Force}$. It may be necessary in some instances to conduct this measure $SF_{EMG\text{-}Force}$ at different known force levels within the same subject to establish the linearity of the force/sEMG relationship, or alternatively to collect data points required to interpolate a non-linear scaling function in the case that this relationship is not predominately linear.

e. With the subject still attached to the device, configure the external force system to provide passive motion for the subject, wherein the device provides the motive forces required to move the subject through their joint movement. Have the subject practice this passive motion while simultaneously observing the sEMG signals that result. Repeat these practices until the sEMG signal ceases to change from one practice passive joint movement to the next. Once the steady-state sEMG signal has been achieved, have the subject execute a passive joint movement while recording the sEMG signal. The parameterized sEMG signal from this movement is referred to as $EMG_{Passive, WB}$.

f. Detach the subject from the device and attach the subject to the device. sEMG sensors should remain unmoved and operational during this change of devices. Disengage the external force system and instruct the subject to move themselves through their maximum joint movement angle. During this movement angle data from the device is synchronously recorded with the sEMG signals that are measured during the movement. Parameterize the sEMG signals from this motion sequence into a single number or index, and this parameterized variable is referred to as $EMG_{Active, Non, WB}$.

g. With the subject still attached to the horizontally configured motion control device, configure the external force system to provide passive motion for the subject, wherein the device provides the motive forces required to move the subject through their movement of the target joint. Have the subject practice this passive motion while simultaneously observing the sEMG signals that result. Repeat these practices until the sEMG signal ceases to change from one practice passive joint movement to the next. Once the steady-state sEMG signal has been achieved, have the subject execute a passive joint movement while recording the sEMG signal. The parameterized sEMG signal from this movement is referred to as $EMG_{Passive, Non\text{-}WB}$.

h. Compute nine quantities, and compare these quantities to those within a demographically stratified normative database of values for the exact same computed values derived from the exact same measurement process and conducted within a specifically defined population of subjects, such as subjects that are pain free, or subjects that have definitively diagnosed muscular pain, etc.

$$Force_{Active,WB} = (EMG_{Active,WB}) \times (SF_{EMG\text{-}Force}) \quad \text{a.}$$

$$Force_{Passive,WB} = (EMG_{Passive,WB}) \times (SF_{EMG\text{-}Force}) \quad \text{b.}$$

$$Force_{Active,Non\text{-}WB} = (EMG_{Active,Non,WB}) \times (SF_{EMG\text{-}Force}) \quad \text{c.}$$

$$Force_{Passive,Non\text{-}WB} = (EMG_{Passive,Non,WB}) \times (SF_{EMG\text{-}Force}) \quad \text{d.}$$

$$\Delta(\text{Active-Passive})_{WB} = (Force_{Active,WB}) - (Force_{Passive,Non\text{-}WB}) \quad \text{f.}$$

$$\Delta(\text{Active-Passive})_{Non\text{-}WB} = (Force_{Active,WB}) - (Force_{Passive,Non\text{-}WB}) \quad \text{g.}$$

$$\Delta(\text{WB-NonWB})_{Active} = (Force_{Active,WB}) - (Force_{Active,Non\text{-}WB}) \quad \text{h.}$$

$$\Delta(\text{WB-NonWB})_{Passive} = (Force_{Passive,WB}) - (Force_{Passive,Non\text{-}WB}) \quad \text{i.}$$

$$\Delta(\text{MAX-MIN}) = (Force_{Active,WB}) - (Force_{Passive,Non\text{-}WB}) \quad \text{j.}$$

i. Use statistical results such as the Percentile within a specific subject population described above to determine if a specific set of values for the above listed set of computed values should be considered normal or dysfunctional. This determination will be made by assigning some statistical threshold, for example 95%, for the purpose of providing a quantitative basis for assessing the presence of muscle dysfunction. If a specific set of values is deemed dysfunctional, then that result must accompany any reports of joint surface motion or reports of the motion of internal joint structures, because then it would be possible that any observed motion dysfunction could be caused by an underlying muscular dysfunction. However if a specific set of values is deemed functional, then that too must accompany any reports of joint surface motion or reports of the motion of internal joint structures, because if "non-dysfunctional" muscular activity is observed then muscle dysfunctions can be ruled out as a potential cause of any observed motion dysfunction. Being able to rule out muscle dysfunctions for subjects in which motion dysfunctions have been observed is extremely useful to clinicians because this can be the basis to indicate one therapy over another, such as indicating non-surgical therapy over surgical therapy.

j. By using these measurements taken at different points in time over a specific time period, it will be possible to determine the extent to which any observed muscle dysfunctions are improving, staying the same, or getting worse. Such observations can be used to assess the "irreversibility" of muscle dysfunctions by correlating any changes to a motion function over time with any specific therapeutic regimen.

k. The results of the above process can be used by the prescriber to determine the exact configuration of the imaging studies, for example.

Heretofore, the above-listed process would have been impossible and it is only the innovation afforded by the first, second and third aspects of the invention that provides for the practicality of this fifth aspect of the invention. It has been the intention of this inventor to develop a diagnostically useful result as a result of the above-listed process, and these requirements then served as the design objectives in the development of the designs for the apparatus and diagnostic method.

The diagnostic method of the present invention requires two different operational processes. There is that process that must be executed for each new test that is prescribed, a description of which directly follows this paragraph, and that process that needs to be done only once during the initial installation, or possibly thereafter after long intervals of usage. This latter process is the apparatus calibration process and is required to initialize the hardware configuration of the apparatus to be compatible with a given testing environment, and also initializing the hardware and software computing processes that are required to enable the flow of testing measurement data between and among the various apparatus components as described in this specification. This calibration process is not described in detail in this specification, as it is highly variable and specific to each testing environment. However the testing process that must be done for each testing subject is given in detail below.

The process that must be done for each testing subject is as follows:
1. Qualify diagnostic testing candidates
2. Prescribe specific testing configuration or configurations
3. Configure testing apparatus
4. Perform testing and process results Each of the above listed process steps is described in detail in the following paragraphs.

Qualify Diagnostic Testing Candidates:
Currently, a subject would be considered a testing candidate if:
 a. The subject has a joint problem or performance issue
 b. The limitations created by the subject's joint problem justify the prescription of a diagnostic test that could involve minimally invasive procedures such as videoflouroscopy/CT scans and/or the administration of pain and/or muscle relaxant drugs
 c. The subject is able to move the problem joint or have the problem joint moved to a sufficient degree that the motion will be detectable in moving diagnostic images Prescribe Specific Testing Configuration:
The process of prescribing a specific testing configuration currently contemplates a prescription algorithm that involves several questions, which are:
 a. Which joint needs to be examined, in which plane of motion, and through which motion?
 b. Should the plane of the fixated body part be at an angle to the plane of the rotated body part?
 c. Should the motion be weight-bearing or non-weight-bearing, or both?
 d. Should the subject be in a bent posture, and if so how?
 e. Should the motion be active or passive on the part of the subject, or both?
 f. Should the motion involve externally generated forces, and if so what kind?
 g. Does pain-associated muscle activity need to be masked?
 h. Does systemic muscle activity need to be reduced?
 i. Will both electromyography measurement as well as imaging data be collected, or is only one of these types of data collection required?

Answering the above-listed questions will yield the specific configuration parameters for the testing apparatus. Currently, there are no investigational data from controlled clinical trials to assist prescribers in answering the above-listed questions. It will only be through the investigational use of the present invention that these questions will be answerable. Therefore for the purpose of this application these diagnostic questions are listed, however the specific clinical insights required to answer them are not included.

Configure Testing Apparatus:
Depending on the outcome of the previous process step in which a specific testing configuration is prescribed, there could be one of several configurations. There are several configuration parameters that, when taken as a group, determine the exact configuration of the testing apparatus. These configuration parameters are:
 a. Posture: Subject can assume a lying, sitting, bent, or standing posture, determined by whether normal, modified, or non-weight-bearing motion is required by prescriber.
 b. Motion parameters: The starting point and ending point, in degrees and/or units of length, and the velocity parameters of the specific joint surface motion that is being studied.
 c. Plane of motion: The plane containing the specific joint motion that is being studied.
 d. Joint Orientation: Orientation of subject's joint with respect to the plane of motion that is being studied
 e. Involvement of external forces:
 f. Electromyography measurement: Measure electromyography for muscles involved in joint motion
 g. Other electric sensor based measurements: Measure other physiological parameters associated with the joint motion and/or underlying fluid dynamics?

Perform Testing and Process Results:
To perform the test, a trained operator operates the configured apparatus to record all images and measurements. If so prescribed by a physician, the subject may be administered muscle relaxant drugs such as metaxalone or diazepam, systemic pain drugs such as oral opioid drugs, and/or local pain drugs such as transdermal lidocaine; the administration of which is for purely the diagnostic purpose of altering the subject's pain and muscle activity in a specific way during testing and image generation.

If specific muscle studies are indicated, then these muscle studies are conducted either before, during, or after the imaging process begins. Once all images and data have been collected and the testing is complete, the next steps are to process these images and data to produce diagnostic measurements, interpret these diagnostic measurements to produce diagnostic results, and transmit these results to the operator and/or the prescriber. The above steps are all accomplished through the normal utilization of existent machines, such as computers and computer networks and require no specific explanation other then the detail given already in this specification section and in the previous discussions of FIG. 1.

The images obtained from the imaging device can, if required, be scaled, prior to analysis to remove inherent distortions or magnifications in that device's image field by the use of corrective geometric transformations in the analysis software. Furthermore, the accuracy of measurement of rotational or translational position and motion data during analysis can be determined by pre-calibration using realistic preset calibration models of the relevant joints. Lastly, the reliability of measuring joint motion parameters using the device in its various configurations, between and within operators and within individual subjects, can be achieved by repeated analysis and/or acquisition of data and image sequences.

FIG. 7 illustrates a expected experimental result from a muscle function study that provide case study data to support the clinical viability of the present invention's capability to detect muscle dysfunction. The sEMG data presented in FIG. 7 were taken from a normal healthy subject during movement of a target joint through a range of motion. The sEMG signal should be completely eliminated as the subject changes from active joint movement to passive joint movement. This same result has been broadly observed across a population of multiple pain free subjects, indicating that the ability to effectively quiet muscle activity by mechanically disengaging motive force-providing muscles is one that should be considered as being within normal physiologic function.

IV. Hypothetical Examples

Hypothetical Example 1

A Weight Bearing Joint

For a weight bearing joint like the neck or spine, there can be useful diagnostic data produced by affecting a comparison of weight bearing motion to non-weight bearing motion. For testing weight bearing motion, the present invention can be configured to be freestanding with both attachment arms occupying the line normal to the floor, and with one attachment arm attached to the patient's head with the other attached to the patient's shoulders. For testing non-weight bearing motion, the attachment arm attached to the shoulders in the previous example could be turned to be parallel to the floor, then attached to a patient on which the patient is lying. The other attachment arm could be attached to the patient's head (as in the previous configuration). Such a configuration would allow for the assessment of motion in a plane parallel to the floor (complete non-weight bearing), or in a plane perpendicular to the floor (partial weight bearing). The results from these tests could then be compared to those taken in full weight bearing, as described at the beginning of this paragraph.

Hypothetical Example 2

A Non-Weight Bearing Joint

For a non-weight bearing joint like the wrist, it would be possible to use a free-standing configuration of the motion control device, with both attachment arms parallel and occupying a plane parallel to the floor. One attachment mechanism could attach to the forearm, and the other to the hand. In this configuration, motion could be tested and compared between that which occupies a plane perpendicular to the floor (up and down wrist movement), and that which occupies a plane parallel to the floor (lateral bending wrist movement). Alternatively, comparisons could be made between active and passive motion on the part of the subject.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of any claim presented and their equivalents be covered thereby.

What is claimed:

1. An apparatus adapted and configured to cause and control joint motion of a patient comprising:
   a) a first motion member configured to engage a patient proximal to a target joint;
   c) a second motion member configured to engage a patient distal to a target joint;
   d) a coupling member configured to connect the first motion member to the second motion member and further adapted to allow rotation of the first and second motion member around an axis;
   e) a dynamic collimator attached to one or more motion members adapted and configured to allow for frame-to-frame changes to a geometry of a non-collimated field of view during imaging of a continuous joint motion
   wherein the apparatus is adapted to be engageable with a medical diagnostic device and wherein the apparatus is further configured to enable the medical diagnostic device to capture frame-to-frame changes of a geometry of a non-collimated field of view during imaging of motion of a joint of the patient during continuous motion of the joint of the patient.

2. The apparatus of claim 1, wherein the apparatus is adapted to be engageable with a medical diagnostic device selected from the group consisting of X-ray scanner, X-ray tube with image intensifier tube, magnetic resonance scanner, infrared camera, computed tomography scanner, ultrasound scanner, electromyography sensor unit, digital camera and camera.

3. The apparatus of claim 1, wherein the apparatus is adapted to be engageable with a medical diagnostic device that is detachably engaged.

4. The apparatus of claim 1, wherein the apparatus is adapted to be engageable with a medical diagnostic device is an electromyography sensor unit with sensors attached to the subject.

5. The apparatus of claim 1, wherein the apparatus is adapted to be engageable with a medical diagnostic device further comprises at least one sensor for capturing patient specific data.

6. The apparatus of claim 1, further comprising a motion control device.

7. The apparatus of claim 1 further comprising a motion controller, wherein the collimator is moveable and adapted to differing geometries during a motion controlled by the motion controller.

8. A system for controlling motion of a target joint during a medical diagnostic procedure comprising:
   an apparatus adapted and configured to selectively cause and control joint motion of a patient having a first motion member configured to engage a patient proximal to a target joint; a second motion member configured to engage a patient distal to a target joint; a coupling member configured to connect the first motion member to the second motion member and further adapted to allow rotation of the first and second motion member around an axis; a dynamic collimator for use in radiographic imaging of mammalian skeletal joints while the mammalian skeletal joints are in motion, adapted and configured to allow for frame-to-frame changes to a geometry of a non-collimated field of view during imaging of the continuous motion of the joints, wherein the apparatus is adapted and configured to engage a medical diagnostic device further configured to capture frame-to-frame changes to a geometry of a non-collimated field of view during imaging of a continuous motion of a joint of the patient; and
   of a medical diagnostic device selected from the group consisting of X-ray scanner, X-ray tube with image intensifier tube, magnetic resonance scanner, infrared camera, computed tomography scanner, ultrasound scanner, electromyography sensor unit, digital camera and camera,
   wherein the target joint can be maintained in a field of view by moving the medical diagnostic device, the apparatus, or a combination thereof.

9. An apparatus adapted and configured to cause and control joint motion of a patient comprising:
   a) a first motion member configured to engage a patient proximal to a target joint;
   c) a second motion member configured to engage a patient distal to a target joint and in moveable communication with the first motion member; and
   d) a collimator in communication with the first and second motions members to provide an indication of movement of the first motion member relative to the second motion member during motion of the joint,
   wherein the apparatus is engageable with a medical diagnostic device and further configured to capture frame-to-frame changes to a geometry of a non-collimated field of view during imaging of a continuous motion of a joint of the patient.

10. The apparatus of claim 9, wherein the apparatus is adapted to be engageable with a medical diagnostic device is selected from the group consisting of X-ray scanner, X-ray tube with image intensifier tube, magnetic resonance scanner, infrared camera, computed tomography scanner, ultrasound scanner, electromyography sensor unit, digital camera and camera.

11. The apparatus of claim 9, wherein the apparatus is adapted to be engageable with a medical diagnostic device is detachably engaged.

12. The apparatus of claim 9, wherein the apparatus is adapted to be engageable with a medical diagnostic device further comprises at least one sensor for capturing patient specific data.

13. The apparatus of claim 9, further comprising a motion control device.

14. The apparatus of claim 9, wherein the collimator is a dynamic collimator.

15. The apparatus of claim 9 further comprising a motion controller, wherein the collimator is moveable and adapted to differing geometries during a motion controlled by the motion controller.

* * * * *